United States Patent [19]

Ojima et al.

[11] Patent Number: 5,276,137
[45] Date of Patent: Jan. 4, 1994

[54] ANALGESIC PEPTIDES WITH A TRIFLUORONORVALINE MODIFICATION

[75] Inventors: Iwao Ojima, Stony Brook, N.Y.; Kazuaki Nakahashi, Takaoka, Japan

[73] Assignee: The Research Foundation of State University of New York, New York, N.Y.

[21] Appl. No.: 630,163

[22] Filed: Dec. 18, 1990

[30] Foreign Application Priority Data

Jun. 19, 1990 [JP] Japan .................. 2-158890

[51] Int. Cl.$^5$ .................. A61K 37/00; A61K 37/02; C07K 5/00; C07K 7/00
[52] U.S. Cl. .................. 530/330; 530/302
[58] Field of Search .................. 514/17; 530/330, 302

[56] References Cited

U.S. PATENT DOCUMENTS

| | | |
|---|---|---|
| 4,261,883 | 4/1914 | Smolarsky . |
| 4,278,596 | 7/1981 | Garsky . |
| 4,322,340 | 3/1982 | Shuman et al. . |
| 4,495,178 | 1/1985 | Hansen, Jr. et al. . |

FOREIGN PATENT DOCUMENTS

005658A1 11/1979 France .
60-36441 8/1979 Japan .

OTHER PUBLICATIONS

Babb et al., J. Organic Chem., vol. 35, No. 5, May 1970, pp. 1438–1440.
Watanabe et al, Biological Abstracts, BA92:21040.
Gesellchen et al., vol. 94, Chemical Abstracts, 1951 p. 315, CA:79491h.
Gesellchen et al., Chemical Abstr. p. 99, vol. 97, 1982, CA:97:956u
Sivanandaiah et al., Chemical Abstr. vol. 110, CA:110:5136c.
J. Hughes et al., Nature, 258, 577–579 (1975).
M. Ueki, Yuki Gosei Kagaku Kyokaishi, Japan, 44, (3), 219–228 (1986).
P. Hansen and B. Morgan, Opiod Peptides: Biology, Chemistry and Genetics, *The Peptides*, vol. 6, Chapter 8 (1984).
A. T. McKnight et al., Eur. J. Pharmacol., 86, 393–402 (1983).

*Primary Examiner*—Merrell C. Cashion, Jr.
*Assistant Examiner*—A.M. Davenport
*Attorney, Agent, or Firm*—Hoffmann & Baron

[57] ABSTRACT

The present invention relates to analgesic enkephalin derivatives represented by the following formula:

Tyr-A$_1$-A$_2$-A$_3$-A$_4$ SEQ ID NO:5     (1)

and the acid salts thereof, wherein Tyr is L-tyrosine, A$_1$ or A$_2$ is a glycine, and that which is not a glycine is an optically active trifluoro amino acid of the formula:

$$\begin{array}{c} (CH_2)_nCF_3 \\ | \\ H_2N-CH-COOH \end{array}$$

wherein n is an integer from 1–3 and m is 1 or 2; A$_3$ is L-Phenylalanine, or N-methyl-(L)-phenylalanine, and A$_4$ is L-Methionine, L-Met-OH, L-Met-ol or L-Met-NH$_2$.

24 Claims, 1 Drawing Sheet

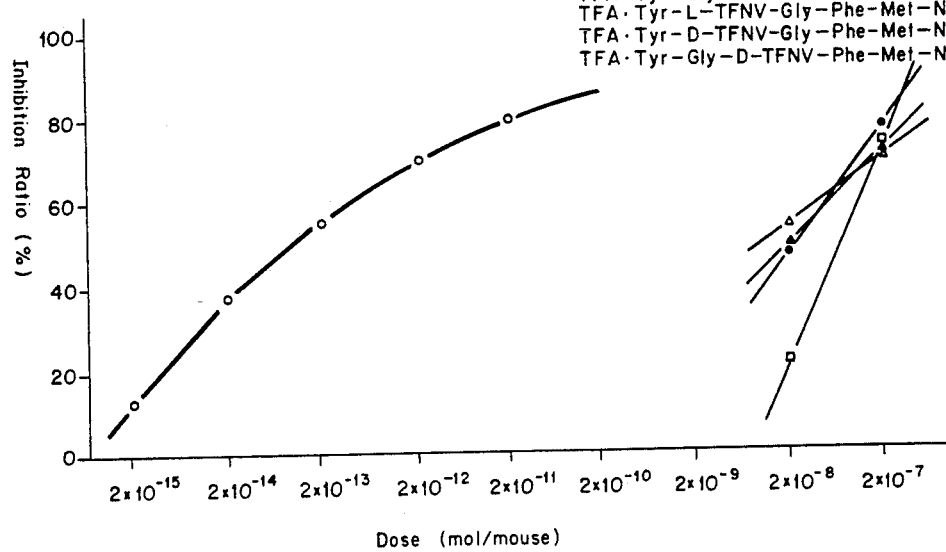

FIG. 1

Legend
- □ ⋯ Met—enkephalin
- ◀ ⋯ TFA·Tyr-Gly-L-TFNV-Phe-Met-NH₂
- ● ⋯ TFA·Tyr-L-TFNV-Gly-Phe-Met-NH₂
- ○ ⋯ TFA·Tyr-D-TFNV-Gly-Phe-Met-NH₂
- △ ⋯ TFA·Tyr-Gly-D-TFNV-Phe-Met-NH₂

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 5 Amino Acids
        ( B ) TYPE: Amino Acid
        ( C ) TOPOLOGY: Linear ( x i ) SEQUENCE DESCRIPTION:SEQ ID NO:1:

Tyr Gly Gly Phe Met
1                 5

(2) INFORMATION FOR SEQ ID NO:2:

(i) SEQUENCE CHARACTERISTICS:
        (A) LENGTH: 5 Amino acids
        (B) TYPE: Amino Acid
        (C) TOPOLOGY: Linear (xi) SEQUENCE DESCRIPTION:SEQ ID NO:2:

Tyr Gly Gly Phe Leu
1                 5

(2) INFORMATION FOR SEQ ID NO:3:

(i) SEQUENCE CHARACTERISTICS:
        (A) LENGTH: 5 Amino acids
        (B) TYPE: Amino Acid
        (C) TOPOLOGY: Linear (ix) FEATURE:
        (A) NAME/KEY: Modified-Site
        (B) LOCATION: 1
        (D) OTHER INFORMATION: /note="

R3

R1-Tyr-

R2
          in which R1 is a lower alkyl, R2 is an aralkyloxycarbonyl
          alkoxycarbonyl and R3 is a lower alkyl."

(ix) FEATURE:
        (A) NAME/KEY: Modified-Site
        (B) LOCATION: 5
        (D) OTHER INFORMATION: /note="Met-ol"

(xi) SEQUENCE DESCRIPTION:SEQ ID NO:3:

Xaa Gly Gly Phe Xaa
1                 5

(2) INFORMATION FOR SEQ ID NO:4:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 1
        (D) OTHER INFORMATION: /note="R1-Tyr
            in which R1 is a lower alkyl."

(ix) FEATURE:
        (A) NAME/KEY: Modified-Site
        (B) LOCATION: 5
        (D) OTHER INFORMATION: /note="Met-ol"

(xi) SEQUENCE DESCRIPTION:SEQ ID NO:4:

Xaa Gly Gly Phe Xaa
1                 5

(2) INFORMATION FOR SEQ ID NO:5:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 2

(D) OTHER INFORMATION: /note="Gly or an
  optically active trifluoro amino acid of the formula:
(CH2)nCF3

H2N-CH-COOH
wherein n is an integer from 1-3."

(ix) FEATURE:
  (A) NAME/KEY: Modified-Site
  (B) LOCATION: 3
  (D) OTHER INFORMATION: /note="Gly or an
    optically active trifluoro amino acid of the formula:
  (CH2)nCF3

H2N-CH-COOH
wherein n is an integer from 1-3."

(ix) FEATURE:
  (A) NAME/KEY: Modified-Site
  (B) LOCATION: 4
  (D) OTHER INFORMATION: /note="L-Phenylalanine, or N-
    methyl-(L)- phenylalanine."

(ix) FEATURE:
  (A) NAME/KEY: Modified-Site
  (B) LOCATION: 5
  (D) OTHER INFORMATION: /note="L-Methionine, L-Met-ol or
    L-Met-NH2 and the acid addition salts thereof."

(xi) SEQUENCE DESCRIPTION:SEQ ID NO:5:

Tyr  Xaa  Xaa  Xaa  Xaa
 1                    5

(2) INFORMATION FOR SEQ ID NO:6:

(i) SEQUENCE CHARACTERISTICS:
    (A) LENGTH: 5 Amino acids
    (B) TYPE: Amino Acid
    (C) TOPOLOGY: Linear (ix) FEATURE:
    (A) NAME/KEY: Modified-Site
    (B) LOCATION: 1
    (D) OTHER INFORMATION: /note="TFAyTyr"

(ix) FEATURE:
    (B) LOCATION: 3
    (D) OTHER INFORMATION: /note="(L)-TFNV"

(ix) FEATURE:
    (A) NAME/KEY: Modified-Site
    (B) LOCATION: 5
    (D) OTHER INFORMATION: /note="Met-NH2"

(xi) SEQUENCE DESCRIPTION:SEQ ID NO:6:

Xaa  Gly  Xaa  Phe  Xaa
 1                    5

(2) INFORMATION FOR SEQ ID NO:7:

(i) SEQUENCE CHARACTERISTICS:
    (A) LENGTH: 5 Amino acids
    (B) TYPE: Amino Acid
    (C) TOPOLOGY: Linear (ix) FEATURE:
    (A) NAME/KEY: Modified-Site
    (B) LOCATION: 1
    (D) OTHER INFORMATION: /note="TFAyTyr"

(ix) FEATURE:
    (A) NAME/KEY: Modified-Site
    (B) LOCATION: 2
    (D) OTHER INFORMATION: /note="(L)-TFNV"

(xi) SEQUENCE DESCRIPTION:SEQ ID NO:7:

Xaa  Xaa  Gly  Phe  Met (2) INFORMATION FOR SEQ ID NO:8:

(i) SEQUENCE CHARACTERISTICS:
    (A) LENGTH: 5 Amino acids
    (B) TYPE: Amino acid
    (C) TOPOLOGY: Linear (ix) FEATURE:
    (A) NAME/KEY: Modified-Site
    (B) LOCATION: 1
    (D) OTHER INFORMATION: /note="TFAyTyr"

(ix) FEATURE:
    (A) NAME/KEY: Modified-Site
    (B) LOCATION: 2
    (D) OTHER INFORMATION: /note="(L)-TFNV"

(ix) FEATURE:
    (A) NAME/KEY: Modified-Site
    (B) LOCATION: 5
    (D) OTHER INFORMATION: /note="Met-NH2"

(xi) SEQUENCE DESCRIPTION:SEQ ID NO:8:

Xaa  Xaa  Gly  Phe  Xaa
    1                    5

(2) INFORMATION FOR SEQ ID NO:9:

(i) SEQUENCE CHARACTERISTICS:
    (A) LENGTH: 5 amino acids
    (B) TYPE: Amino Acid
    (C) TOPOLOGY: Linear (ix) FEATURE:
    (A) NAME/KEY: Modified-Site
    (B) LOCATION: 1
    (D) OTHER INFORMATION: /note="TFAyTyr"

(ix) FEATURE:
    (A) NAME/KEY: Modified-Site
    (B) LOCATION: 3
    (D) OTHER INFORMATION: /note="(L)-TFNV"

(xi) SEQUENCE DESCRIPTION:SEQ ID NO:9:

Xaa  Gly  Xaa  Phe  Met
    1                    5

(2) INFORMATION FOR SEQ ID NO:10:

(i) SEQUENCE CHARACTERISTICS:
    (A) LENGTH: 4 Amino acids
    (B) TYPE: Amino acid
    (C) TOPOLOGY: Linear (ix) FEATURE:
    (A) NAME/KEY: Modified-Site
    (B) LOCATION: 1
    (D) OTHER INFORMATION: /note="FMOC-Gly"

(ix) FEATURE:
    (A) NAME/KEY: Modified-Site
    (B) LOCATION: 2
    (D) OTHER INFORMATION: /note="(L)-TFNV"

(ix) FEATURE:
    (A) NAME/KEY: Modified-Site
    (B) LOCATION: 4
    (D) OTHER INFORMATION: /note="Met NH Resin complex."

(xi) SEQUENCE DESCRIPTION:SEQ ID NO:10:

Xaa  Xaa  Phe  Xaa
    1

( 2 ) INFORMATION FOR SEQ ID NO:11:

( i ) SEQUENCE CHARACTERISTICS:
        ( A ) LENGTH: 4 Amino acids
        ( B ) TYPE: Amino acid
        ( C ) TOPOLOGY: Linear ( i x ) FEATURE:
        ( A ) NAME/KEY: Modified-Site
        ( B ) LOCATION: 2
        ( D ) OTHER INFORMATION: /note="(L)-TFNV"

( i x ) FEATURE:
        ( A ) NAME/KEY: Modified-Site
        ( B ) LOCATION: 4
        ( D ) OTHER INFORMATION: /note="Met-NH-Resin complex."

( x i ) SEQUENCE DESCRIPTION:SEQ ID NO:11:

Gly  Xaa  Phe  Xaa
        1

( 2 ) INFORMATION FOR SEQ ID NO:12:

( i ) SEQUENCE CHARACTERISTICS:
        ( A ) LENGTH: 5 Amino acids
        ( B ) TYPE: Amino Acid
        ( C ) TOPOLOGY: Linear ( i x ) FEATURE:
        ( A ) NAME/KEY: Modified-Site
        ( B ) LOCATION: 1
        ( D ) OTHER INFORMATION: /note="FmocyTyr"

( i x ) FEATURE:
        ( A ) NAME/KEY: Modified-Site
        ( B ) LOCATION: 3
        ( D ) OTHER INFORMATION: /note="(L)-TFNV"

( i x ) FEATURE:
        ( A ) NAME/KEY: Modified-Site
        ( B ) LOCATION: 5
        ( D ) OTHER INFORMATION: /note="Met-NH-Resin complex."

( x i ) SEQUENCE DESCRIPTION:SEQ ID NO:12:

Xaa  Gly  Xaa  Phe  Xaa
        1                    5

( 2 ) INFORMATION FOR SEQ ID NO:13:

( i ) SEQUENCE CHARACTERISTICS:
        ( A ) LENGTH: 4 Amino acids
        ( B ) TYPE: Amino Acid
        ( C ) TOPOLOGY: Linear ( i x ) FEATURE:
        ( A ) NAME/KEY: Modified-Site
        ( B ) LOCATION: 1
        ( D ) OTHER INFORMATION: /note="FMOC-(L)-TFNV"

( i x ) FEATURE:
        ( A ) NAME/KEY: Modified-Site
        ( B ) LOCATION: 4
        ( D ) OTHER INFORMATION: /note="Met-NH-Resin complex."

( x i ) SEQUENCE DESCRIPTION:SEQ ID NO: 13:

Xaa  Gly  Phe  Xaa
        1

( 2 ) INFORMATION FOR SEQ ID NO:14:

( i ) SEQUENCE CHARACTERISTICS:
        ( A ) LENGTH: 4 Amino acids
        ( B ) TYPE: Amino acid
        ( C ) TOPOLOGY: Linear ( i x ) FEATURE:

(A) NAME/KEY: Modified-Site
(B) LOCATION: 1
(D) OTHER INFORMATION: /note="(L)-TFNV"

(ix) FEATURE:
(B) LOCATION: 4
(D) OTHER INFORMATION: /note="Met-NH-Resin complex."

(xi) SEQUENCE DESCRIPTION:SEQ ID NO:14:

Xaa Gly Phe Xaa
1

(2) INFORMATION FOR SEQ ID NO:15:

(i) SEQUENCE CHARACTERISTICS:
(A) LENGTH: 5 Amino acids
(B) TYPE: Amino acid
(C) TOPOLOGY: Linear (ix) FEATURE:
(A) NAME/KEY: Modified-Site
(B) LOCATION: 1
(D) OTHER INFORMATION: /note="FmocyTyr"

(ix) FEATURE:
(A) NAME/KEY: Modified-Site
(B) LOCATION: 2
(D) OTHER INFORMATION: /note="(L)-TFNV"

(ix) FEATURE:
(A) NAME/KEY: Modified-Site
(B) LOCATION: 5
(D) OTHER INFORMATION: /note="Met-NH Resin complex."

(xi) SEQUENCE DESCRIPTION:SEQ ID NO:15:

Xaa Xaa Gly Phe Xaa
1                 5

(2) INFORMATION FOR SEQ ID NO:16:

(i) SEQUENCE CHARACTERISTICS:
(A) LENGTH: 5 Amino acids
(B) TYPE: Amino acid
(C) TOPOLOGY: Linear (ix) FEATURE:
(A) NAME/KEY: Modified-Site
(B) LOCATION: 3
(D) OTHER INFORMATION: /note="(L)-TFNV"

(ix) FEATURE:
(A) NAME/KEY: Modified-Site
(B) LOCATION: 5
(D) OTHER INFORMATION: /note="Met-NH2"

(xi) SEQUENCE DESCRIPTION:SEQ ID NO:16:

Tyr Gly Xaa Phe Xaa
1                 5

(2) INFORMATION FOR SEQ ID NO:17:

(i) SEQUENCE CHARACTERISTICS:
(A) LENGTH: 5 Amino acids
(B) TYPE: Amino acid
(C) TOPOLOGY: Linear (ix) FEATURE:
(A) NAME/KEY: Modified-Site
(B) LOCATION: 1
(D) OTHER INFORMATION: /note="R1-NH-Tyr, wherein R1 is
hydrogen, methyl, ethyl, propyl 2-methyl-2-penteryl, 2-
methyl-1- pentenyl, cyclopropylmethyl, or cyclobutylmethyl (ix) FEATURE:
(A) NAME/KEY: Modified-Site
(B) LOCATION: 2

(D) OTHER INFORMATION: /note="N-(D)-Ser, wherein R2 is

R2
hydrogen or methyl."

(ix) FEATURE:
    (A) NAME/KEY: Modified-Site
    (B) LOCATION: 4
    (D) OTHER INFORMATION: /note="N-Phe, wherein R3 is R3
hydrogen or methyl."

(ix) FEATURE:
    (A) NAME/KEY: Modified-Site
    (B) LOCATION: 5
    (D) OTHER INFORMATION: /note="N-(D)-Ser-X, wherein R4

R4
is hydrogen or methyl and X is OH, NH2 or NHCnH2n'where
n is 1, 2, 3, or 4; OR3 or CH2OR3, where R3 is a hydrogen
lower alkyl of from 1 to 4 carbon atoms."

(xi) SEQUENCE DESCRIPTION: SEQ ID NO:17:

Xaa Xaa Gly Xaa Xaa
1                 5

(2) INFORMATION FOR SEQ ID NO:18:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 2
        (D) OTHER INFORMATION: /note="(D)-Ala"

(ix) FEATURE:
        (A) NAME/KEY: Modified-Site
        (B) LOCATION: 4
        (D) OTHER INFORMATION: /note="Phe or pf-Phe."

(ix) FEATURE:
        (A) NAME/KEY: Modified-Site
        (B) LOCATION: 5
        (D) OTHER INFORMATION: /note="B-NH-Cn-H2n-Y, wherein
            B is Met, Leu, monofluoro-Leu, Pro, Monofluoro-Pro or a
            single bond; Y is a halogen, a 1-4C alkyl mono- or
            polysubstituted by a halogen or by a phenyl, an amino
            group - NHX, a sulphonamido group - NHSO2X, a carbonyl
            group - COX or an acylamino group - NHCO(CH2)mX; X is a
            halogen, a 1- 4C alkyl mono or polysubstituted halogen,
            a phenyl, or a halo substituted benzhydryl, an alpha or b
            naphthyl, or a residue of a mono- or polycyclic group cho
            from thiopene, quinoline, isoquinoline, acridine, and
            pyridine, wherein m, is 0-4 and n is 0-6."

(xi) SEQUENCE DESCRIPTION: SEQ ID NO: 18:

Tyr Xaa Gly Xaa Xaa
1                 5

(2) INFORMATION FOR SEQ ID NO:19:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 1
        (D) OTHER INFORMATION: /note="TFAyTyr"

(ix) FEATURE:
        (A) NAME/KEY: Modified-Site
        (B) LOCATION: 2

(D) OTHER INFORMATION: /note="(D)-TFNV"

(ix) FEATURE:
    (A) NAME/KEY: Modified-Site
    (B) LOCATION: 5
    (D) OTHER INFORMATION: /note="Met-NH2"

(xi) SEQUENCE DESCRIPTION: SEQ ID NO: 19:

Xaa  Xaa  Gly  Phe  Xaa
   1                        5

(2) INFORMATION FOR SEQ ID NO:20:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 1
        (D) OTHER INFORMATION: /note="TFAyTyr"

(ix) FEATURE:
        (A) NAME/KEY: Modified-Site
        (B) LOCATION: 3
        (D) OTHER INFORMATION: /note="(D)-TFNV"

(ix) FEATURE:
        (A) NAME/KEY: Modified-Site
        (B) LOCATION: 5
        (D) OTHER INFORMATION: /note="Met-NH2"

(xi) SEQUENCE DESCRIPTION: SEQ ID NO: 20:

Xaa  Xaa  Gly  Phe  Xaa
   1                        5

(2) INFORMATION FOR SEQ ID NO:21:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 1
        (D) OTHER INFORMATION: /note="TFAyTyr"

(ix) FEATURE:
        (A) NAME/KEY: Modified-Site
        (B) LOCATION: 2
        (D) OTHER INFORMATION: /note="(D)-TFNV"

(xi) SEQUENCE DESCRIPTION: SEQ ID NO: 21:

Xaa  Xaa  Gly  Phe  Xaa
   1                        5

(2) INFORMATION FOR SEQ ID NO:22:

(i) SEQUENCE CHARACTERISTICS:
        (A) LENGTH: 5 Amino acids
        (B) TYPE: Amino acid
        (C) TOPOLOGY: Linear (ix) FEATURE:
        (A) NAME/KEY: Modified-Site
        (B) LOCATION: 2
        (D) OTHER INFORMATION: /note="(D)-TFNV"

(ix) FEATURE:
        (A) NAME/KEY: Modified-Site
        (B) LOCATION: 5
        (D) OTHER INFORMATION: /note="Met-NH2"

(xi) SEQUENCE DESCRIPTION: SEQ ID NO: 22:

Xaa    Xaa    Gly    Phe    Xaa
        1                            5

( 2 ) INFORMATION FOR SEQ ID NO:23:

( i ) SEQUENCE CHARACTERISTICS:
        ( A ) LENGTH: 4 Amino acids
        ( B ) TYPE: Amino acid
        ( C ) TOPOLOGY: Linear ( i x ) FEATURE:
        ( A ) NAME/KEY: Modified-Site
        ( B ) LOCATION: 1
        ( D ) OTHER INFORMATION: /note="Fmoc"

( i x ) FEATURE:
        ( A ) NAME/KEY: Modified-Site
        ( B ) LOCATION: 2
        ( D ) OTHER INFORMATION: /note="(D)-TFNV"

( i x ) FEATURE:
        ( A ) NAME/KEY: Modified-Site
        ( B ) LOCATION: 4
        ( D ) OTHER INFORMATION: /note="Met-NH-Resin complex."

( x i ) SEQUENCE DESCRIPTION: SEQ ID NO: 23:

Xaa    Xaa    Phe    Xaa
        1

( 2 ) INFORMATION FOR SEQ ID NO:24:

( i ) SEQUENCE CHARACTERISTICS:
        ( A ) LENGTH: 5 Amino acids
        ( B ) TYPE: Amino acid
        ( C ) TOPOLOGY: Linear ( i x ) FEATURE:
        ( A ) NAME/KEY: Modified-Site
        ( B ) LOCATION: 1
        ( D ) OTHER INFORMATION: /note="Fmoc"

( i x ) FEATURE:
        ( A ) NAME/KEY: Modified-Site
        ( B ) LOCATION: 3
        ( D ) OTHER INFORMATION: /note="(D)-TFNV"

( i x ) FEATURE:
        ( A ) NAME/KEY: Modified-Site
        ( B ) LOCATION: 5
        ( D ) OTHER INFORMATION: /note="Met-NH-Resin complex."

( x i ) SEQUENCE DESCRIPTION: SEQ ID NO: 24:

Xaa    Gly    Xaa    Phe    Xaa
        1                            5

( 2 ) INFORMATION FOR SEQ ID NO:25:

( i ) SEQUENCE CHARACTERISTICS:
        ( A ) LENGTH: 4 Amino acids
        ( B ) TYPE: Amino acid
        ( C ) TOPOLOGY: Linear ( i x ) FEATURE:
        ( A ) NAME/KEY: Modified-Site
        ( B ) LOCATION: 2
        ( D ) OTHER INFORMATION: /note="(D)-TFNV"

( i x ) FEATURE:
        ( A ) NAME/KEY: Modified-Site
        ( B ) LOCATION: 4
        ( D ) OTHER INFORMATION: /note="Met-NH-Resin complex."

( x i ) SEQUENCE DESCRIPTION: SEQ ID NO: 25:

Gly    Xaa    Phe    Xaa
        1

(2) INFORMATION FOR SEQ ID NO:26:

(i) SEQUENCE CHARACTERISTICS:
    (A) LENGTH: 6 Amino acids
    (B) TYPE: Amino acid
    (C) TOPOLOGY: Linear (ix) FEATURE:
    (A) NAME/KEY: Modified-Site
    (B) LOCATION: 1
    (D) OTHER INFORMATION: /note="Fmoc"

(ix) FEATURE:
    (A) NAME/KEY: Modified-Site
    (B) LOCATION: 4
    (D) OTHER INFORMATION: /note="(D)-TFNV"

(ix) FEATURE:
    (A) NAME/KEY: Modified-Site
    (B) LOCATION: 6
    (D) OTHER INFORMATION: /note="Met-NH-Resin complex."

(xi) SEQUENCE DESCRIPTION: SEQ ID NO: 26:

Xaa  Tyr  Gly  Xaa  Phe  Xaa
    1                   5

(2) INFORMATION FOR SEQ ID NO:27:

(i) SEQUENCE CHARACTERISTICS:
    (A) LENGTH: 4 Amino acids
    (B) TYPE: Amino acid
    (C) TOPOLOGY: Linear (ix) FEATURE:
    (A) NAME/KEY: Modified-Site
    (B) LOCATION: 1
    (D) OTHER INFORMATION: /note="Fmoc"

(ix) FEATURE:
    (A) NAME/KEY: Modified-Site
    (B) LOCATION: 2
    (D) OTHER INFORMATION: /note="(L)-TFNV"

(ix) FEATURE:
    (A) NAME/KEY: Modified-Site
    (B) LOCATION: 4
    (D) OTHER INFORMATION: /note="Met-NH-Resin complex."

(xi) SEQUENCE DESCRIPTION: SEQ ID NO: 27:

Xaa  Xaa  Phe  Xaa
    1

ANALGESIC PEPTIDES WITH A TRIFLUORONORVALINE MODIFICATION

BACKGROUND OF THE INVENTION

The present invention relates to analgesic peptides, and, in particular peptidase-resistant pentapeptides.

Enkephalins are naturally occurring pentapeptides. There are two known enkephalins. Methionine-enkephalins have the amino acid sequence (1):

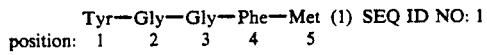

Tyr—Gly—Gly—Phe—Met (1) SEQ ID NO: 1
position: 1    2    2    4    5

Leucine-enkephalins have the amino acid sequence (2):

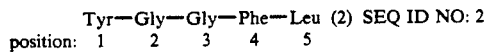

Tyr—Gly—Gly—Phe—Leu (2) SEQ ID NO: 2
position: 1    2    3    4    5

Both enkephalins have strong analgesic activity. (J. Hughes et al., Nature, 258 577 (1975). However, when naturally occurring enkephalins are administered intravenously, they tend to be digested by endogenous peptidases, hence, intravenously administered enkephalins are of limited medical use. It has been reported that cleavage of the peptide bond between the tyrosine residue at the 1 position and the glycine residue at the 2 position results in the complete loss of analgesic activity. (M. Ueki, Yuki Gosei Kagaku Kyokaishi, Japan, 44 (3), 219 (1986).

Extensive structural modifications of the basic enkephalin compound have been made. While some of these modified compounds have demonstrated enhanced activity, none of the modified compounds involve the use of a trifluoro amino acid in a pentapeptide sequence. Nor, do they suggest trifluoro amino acid containing enkephalin analogs. For example, see P. Hansen and B. Morgan, "Opioid Petpides: Biology, Chemistry and Genetics," The Peptides, Vol. 6, Chapter 8 (1984).

The cleavage of peptidases will be inhibited if the enzymes do not recognize the above-referenced specific amino acid residues in the substrate peptide. Methionine-enkephalins and their hexapeptide, heptapeptide and octapeptide C-terminus extensions, have been prepared and used with pedtidase inhibitors. While some of these compounds have been effective, none of the compounds involve or suggest the use of a trifluoro amino acid in a pentapeptide sequence to inhibit the action of endogenous peptidases. For example, see A. T. McKnight et al., Eur. J. Pharmacol., 86, 393 (1983).

U.S. Pat. No. 4,278,596 to Garsky discloses analgesic pentapeptides of the formula:

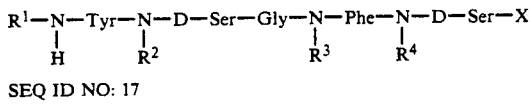

SEQ ID NO: 17 wherein $R^1$ is hydrogen, methyl, ethyl, propyl, 2-methyl-2-pentenyl, 2-methyl-1-pentenyl, cyclopropylmethyl, or cyclobutylmethyl; $R^2$, $R^3$, and $R^4$ are, independently, hydrogen or methyl; and wherein X is —OH, —NH$_2$, —NHC$_n$H$_{2n+1}$ (where n is 1, 2, 3, or 4), —OR$^3$, or CH$_2$OR$^3$, where $R^3$ is a hydrogen or lower alkyl of from 1 to 4 carbon atoms; and the pharmaceutically acceptable salts thereof. Garsky does not suggest or disclose trifluoro-enkephalin analogs.

U.S. Pat. No. 4,261,883 to Smolarsky discloses N-aralkyl and N-aralkenyl substituted enkephalinamide analogs having analgesic and opioid properties. The analgesic comprises a short chain polypeptide having at least three members. The short chain polypeptide terminates in an N-substituted carboxy amide. Wherein the substituent is an aryl group of from 0 to 1 site of ethylenic unsaturation (i.e., aralkyl and aralkenyl). The polypeptide chain includes at the carboxy end, going from amine to carboxy, at least a tripeptide group L-tyr-D-ala-gly. Smolarsky does not disclose or suggest trifluoro enkephalin analogs.

Japanese Patent No. J5 6036-441 discloses the production of enkephalin derivatives by reacting a protected enkephalin derivative with trifluoromethane sulphonic acid. In the method of production of the enkephalin derivatives, compounds of formula (I) are reacted with trifluoromethane sulphonic acid (TFMA; a deprotecting agent) and thioether derivatives of formula II.

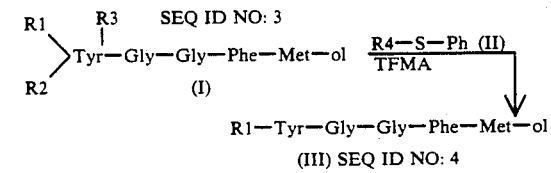

In the above compounds, $R_1$ is a lower alkyl, $R_2$ is an aralkyloxycarbonyl or alkoxycarbonyl and $R_3$ and $R_4$ are lower alkyls. Japanese Patent J5 6036-441 does not disclose or suggest analgesic trifluoro enhephalin analogs.

European Patent 005658 discloses enkephalin peptide analogs (and their acid addition salts) of the formula:

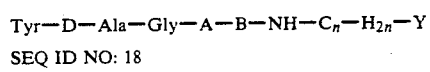

Tyr—D—Ala—Gly—A—B—NH—C$_n$—H$_{2n}$—Y

SEQ ID NO: 18 wherein A is Phe or pF-Phe; B is Met, Leu, monofluoro-leu, Pro, monofluoro-Pro or a single bond; Y is a halogen, a 1-4C alkyl mono- or polysubstituted by a halogen or by a phenyl, an amino group —NHX, a sulphonamido group —NHSO$_2$X, a carbonyl group —COX or an acylamino group —NHCO(CH$_2$)$_m$X; X is a halogen, a 1-4C alkyl mono or polysubstituted halogen, a phenyl, or a halo substituted benzhydryl, an alpha or beta naphthyl, or a residue of mono- or polycyclic group chosen from thiophene, quinoline, isoquinoline, acridine and pyridine, wherein m is 0-4 and n is 0-6. The European Patent does not disclose or suggest trifluoro enkephalin analogs.

It is, therefore, an object of the present invention to provide analgesic trifluoro enkephalin analogs.

It is another object of the present invention to provide enkephalin analogues which can effectively be administered intravenously and are peptidase resistant.

It is yet another object of the present invention to provide enkephalin analogues with enhanced analgesic activity.

Other and further objects will become apparent to those skilled in the art upon reading the present specification, and it is not intended in any way to restrict the scope of the invention by setting forth the objects above.

SUMMARY OF THE INVENTION

These and other objects of the present invention are achieved by the present invention which provides peptidase resistant analgesic pentapeptides.

The present invention includes Met-enkephalin derivatives of the general structural formula:

Tyr—$A_1$—$A_2$—$A_3$—$A_4$   SEQ ID NO: 5 and the acid addition salts thereof,
wherein, $A_1$ or $A_2$ is a glycine residue and that which is not a glycine residue is the residue of an optically compound of the formula:

$$\underset{H_2N-CH-COOH}{\overset{(CH_2)_nCF_3}{|}}$$

wherein n is an integer from 1-3; $A_3$ is L-Phenylalanine, or N-methyl-(L)-phenylalanine, and $A_4$ is L-Methionine, L-Met-ol or L-Met-$NH_2$.

Compounds of the present invention include, for example:

| | |
|---|---|
| TFA.Tyr—Gly—(L)—TFNV—Phe—Met—$NH_2$; | SEQ ID NO: 6 |
| TFA.Tyr—(L)—TFNV—Gly—Phe—Met; | SEQ ID NO: 7 |
| TFA.Tyr—(L)—TFNV—Gly—Phe—Met—$NH_2$; | SEQ ID NO: 8 |
| TFA.Tyr—(D)—TFNV—Gly—Phe—Met—$NH_2$; | SEQ ID NO: 19 |
| TFA.Tyr—Gly—(D)—TFNV—Phe—Met—$NH_2$; | SEQ ID NO: 20 |
| TFA.Tyr—Gly—(L)—TFNV—Phe—Met; and | SEQ ID NO: 9 |
| TFA.Tyr—(D)—TFNV—Gly—Phe—Met | SEQ ID NO: 21 |

An advantage of the present invention is that it provides analgesic activity which is up to five orders of magnitude (i.e., $10^5$) greater than that of the parent methionine-enkephalin pentapeptide.

A further advantage of the present invention is that it provides an analgesic pentapeptide which is resistant to digestion by endogenous peptidases.

A still further advantage of the present invention is that it can easily be made using conventional processes such as, for example, solid phase peptide synthesis or solution phase peptide synthesis.

Yet another advantage of the present invention is that it can be effectively administered intravenously.

For a better understanding of the present invention, reference is made to the following description, taken in conjunction with the following figure, the scope of which is pointed out in the appended claims.

BRIEF DESCRIPTION OF THE DRAWING

FIG. 1 is a graph detailing the dose-response curves of trifluoronorvaline containing Met-enkephalin analogues and Met-enkephalin.

DETAILED DESCRIPTION OF THE PREFERRED EMBODIMENTS

The present invention relates to new enkephalin derivatives and analgesics. More particularly, this invention relates to new enkephalin derivatives, and the acid addition salts thereof, having the residue of an optically active trifluoro amino acid replacing a glycine residue in the chemical structure of an endogenous enkephalin. The trifluoro Met-enkephalin analogues, and the acid addition salts thereof, provide analgesic activity as much as five orders of magnitude (i.e., $10^5$) greater than that of the parent methionine-enkephalin pentapeptide sequence.

The present invention includes new enkephalin derivatives of the general structural formula (3):

Tyr—$A_1$—$A_2$—$A_3$—$A_4$   (3)   SEQ ID NO: 5 wherein, $A_1$ or $A_2$ is a glycine residue and that which is not a glycine residue is the residue of an optically active trifluoro amino acid of the formula:

$$\underset{H_2N-CH-COOH}{\overset{(CH_2)_nCF_3}{|}} \quad (4)$$

wherein n is an integer from 1-3; $A_3$ is L-Phenylalanine, or N-methyl-(L)-phenylalanine, and $A_4$ is L-Methionine, L-Met-ol or L-Met-$NH_2$ and the acid addition salts thereof.

Preferably, n is 2 and the optically active trifluoro amino acid is 5,5,5-trifluoronorvaline. The substitution of the optically active trifluoro amino acid for glycine, at the 2 or 3 position in an enkephalin molecule, provides a new group of enkephalin derivatives which have far greater analgesic activity than the naturally occurring enkephalins.

The compounds of the present invention, can be manufactured by peptide synthesis processes such as, for example, solid-phase peptide syntheses and solution-phase peptide syntheses.

In the solid phase peptide synthesis process, the order in which the amino acids are coupled is not critical. The manufacture of the desired peptides by solid-phase peptide synthesis can easily be performed using commercially available peptide synthesizers (such as, for example, the RAMPS ™ system available from DuPont). First, an N-terminus protected amino acid is prepared with a proper protecting group, such as an Fmoc group, which is sequentially attached with a polymer support. The protecting group is then removed. Successive coupling reactions, of an N-protected amino acid and deprotections are done in a similar manner to produce the enkephalin analogues of the present invention.

The solution phase peptide syntheses can be performed with a conventional coupling method using a C-terminus protected amino acid and an N-terminus protected amino acid in the presence of a coupling reagent such as, for example, dicyclohexylcarbodiimide in an appropriate solvent such as, for example, DFM, tetrahydofuran and halogenated organic solvents.

The compounds of the present invention include the pharmaceutically acceptable inorganic and organic acid addition salts of trifluoronorvaline containing Met-enkephalin analogues. Such salts can be derived from a variety of inorganic and organic acids such as, for example, hydrochloric, sulfuric, citric, lactic, oxalic, maleic, succinic, tartaric, acetic, trifluoroacetic, salicylic, ascorbic and related acids. The acid addition salts tend to be more stable than their counterparts. If desired, the acid group may be removed from the compound by treatment with an appropriate base.

Compounds of the present invention include, for example, the following compounds:

| | |
|---|---|
| TFA.Tyr—Gly—(L)—TFNV—Phe—Met—$NH_2$; | SEQ ID NO: 6 |
| TFA.Tyr—(L)—TFNV—Gly—Phe—Met; | SEQ ID NO: 7 |
| TFA.Tyr—(L)—TFNV—Gly—Phe—Met—$NH_2$; | SEQ ID NO: 8 |
| TFA.Tyr—(D)—TFNV—Gly—Phe—Met—$NH_2$; | SEQ ID NO: 19 |

-continued

| | |
|---|---|
| TFA.Tyr—Gly—(D)—TFNV—Phe—Met—NH₂; | SEQ ID NO: 20 |
| TFA.Tyr—Gly—(L)—TFNV—Phe—Met; | SEQ ID NO: 9 |
| Tyr.(D)—TFNV—Gly—Phe—Met—NH₂; and | SEQ ID NO: 22 |
| TFA.Tyr—(D)—TFNV—Gly—Phe—Met | SEQ ID NO: 21 |

In this specification, the following abbreviations, most of which are well known and are commonly used in the art, are employed:

| | |
|---|---|
| Tyr: | L-tyrosine |
| Gly: | glycine |
| Phe: | L-phenylalanine |
| Met: | L-methionine |
| Leu: | L-leucine |
| L-TFNV: | S (or L) -5,5,5-trifluoronorvaline |
| D-TFNV: | R (or D) -5,5,5-trifluoronorvaline |
| DMF: | dimethylformamide |
| Fmoc: | fluorenylmethoxycarbonyl residue |
| Fmoc-Cl: | fluorenylmethoxycarbonyl chloride |
| TFA: | trifluoroacetic acid |
| Met-ol: | Methionineol |
| N—Me—Phe: | N-Methyl-(L)-Phenylalanine |
| Met—NH₂: | Methiamide |
| Pfp: | Pentafluorophenyl |

The compounds of the present invention can be administered alone or in combination with pharmaceutically acceptable carriers. The proportion of the pharmaceutically acceptable carriers is determined by the solubility and chemical nature of the compound, the selected route of administration, and standard pharmaceutical practice. Suitable pharmaceutical carrier solutions include, for example, dextrose solutions, sodium chloride solutions (saline), sterile water and buffer solutions. A preferred pharmaceutical carrier includes a phosphate buffer solution.

Preferred compositions are those suitable for parenteral administration such as, for example, intramuscular, subcutaneous, or intravenous administration. These include sterile, injectable solutions or suspensions, and sterile injectable depot or slow-release formulations. Particularly, convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as, for example, binders, lubricants, inert diluents, lubricating agents, surface active agents, buffers, flavoring agents, thickeners, preservatives, dispensing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 4 μg to about 17 μg per kilogram body weight of the recipient, and preferably, from about 8 μg to about 17 μg per kilogram body weight, when administered intramuscularly or subcutaneously, and from about 7 μg to about 14 μg per kilogram body weight of the recipient, and, preferably, from about 4 μg to about 8 μg per kilogram body weight, when administered intravenously.

When administered orally, the dosage generally will range from about 20 ng to about 50 ng per kilogram body weight of the recipient, and preferably, from about 15 ng to about 45 ng per kilogram body weight, and more preferably, from about 12 ng to about 24 ng per kilogram body weight.

The following examples are provided to illustrate the preparation and activity of certain compounds of the present invention. It will be apparent to those skilled in the art that many modifications of these embodiments of the present invention can be carried out.

EXAMPLES

Example I

N-Acetyl-5,5,5-Trifluoronorvaline (N-Ac-TFNV)

A 300 ml autoclave was charged with 3-(trifluoromethyl)propanal (1.26g, 10 mmol), acetamide (885 mg, 15 mmol), cobalt carbonyl ($CO_2(CO)_8$; 171 mg, 0.5 mmol), and dioxane (10 ml). The atmosphere was replaced with carbon monoxide and pressurized to 1,500 psi with carbon monoxide and hydrogen ($CO:H_2=1:1$) at room temperature. The autoclave was heated at 120° C. for 12 hours with stirring. The gases were then carefully purged out at 0° C. To the reaction mixture were added 5% $Na_2CO_3$ (50 ml) and ethyl acetate (30 ml) with stirring. The aqueous layer was separated and the organic layer was further extracted with water. The combined aqueous solution was acidified with phosphoric acid and extracted with ethyl acetate. The extract was dried over anhydrous $MgSO_4$ and Norit TM. After filtration and removal of the solvent, N-Ac-TFNV was obtained as a white solid (1.70g, 80%), mp 119°-122° C.; $^1$H NMR (DMSO-$d_6$/TMS) δ1.86 (ε, 3H), 1.70-2.00 (m, 2H), 2.20-2.40 (m, 2H), 4.27 (m, 1 H), 8.21 (d, J=7.8 Hz, 1H); $^{19}$F NMR (DMSO-$d_6$/CF$_3$Cl) δ-64.5 (t, J-9.7 Hz); IR (KBr disk) 3365 (NH), 1720 (C=O), 1610 (C=O), 1550 (δNH). Anal. Calcd for $C_7H_{10}F_3NO_3$: C, 39.44; II, 4.73; N, 6.57. Found: C, 39.17; H,4,73; N, 6.82.

Example II (S)-5,5,5-Trifluoronorvaline ((S)-TFNV)

A solution of N-Ac-TFNV (5.00g, 23.5 mmol) in water (20 ml) was adjusted to have a pH of 7. Porcine kidney acylase I (15 mg, 850 unit/mg) was added at 25° C. The reaction mixture was kept at 25° C. for 14 hours with stirring. The resulting precipitate was collected on a glass filter, redissolved in water, and purified by being passed through a Waters reversed phase filter, Sep-Pak C$_{18}$ (eluent: water). The removal of water in vacuo to dryness gave (S)-TFNV (1.61g, 40%): $[\alpha]_D^{20}+7.2°$ (c 1.5, H$_2$O).

Example III

(R)-5,5,5-Trifluoronorvaline ((R)-TFNV)

The filtrate of the reaction mixture was acidified with 1N HCl to have a pH of 3.0 and extracted with ethyl acetate. After drying over anhydrous MgSO4, the solvent was removed to give (R)-Ac-TFNV as a white solid (1.25g, 25%): $[\alpha]^{20}$ −0.6° (c 1.5, EtOAc). The hydrolysis of (R)-Ac-TFNV (1.00g, 4.69 mmol) with 3N HCl under reflux for 3 hours was followed by neutralization with concentrated aqueous ammonia. The resulting precipitate was collected on a glass filter, re-dissolved in water, and purified by being passed through a Waters reversed phase filter, Sep-Pak $C_{18}$ (eluent: water). The removal of water in vacuo to dryness gave (R)-TFNV (669 mg, 83.4%) as a white solid: $[\alpha]_D^{20}$ −6.8° (C 0.58, H2O).

Example IV

N-Fluorenylmethoxycarbonyl-S-5,5,5-trifluoronorvaline (Fmoc-(S)-TFNV)

(S)-TFNV (650 mg, 3.8 mmol) was dissolved in 20 ml of water together with sodium carbonate (1.01 mg, 9.5 mmol). Fmoc-Cl (938 mg, 3.8 mmol) in 10 ml of dioxane was added dropwise to the aqueous solution, with vigorous stirring, at 0° C. over a period of 30 minutes. The stirring was continued for 4 hours at 0° C. and 40 ml of water was added to dissolve some precipitation. The reaction mixture was stirred for 15 hours at room temperature, then poured into 300 ml of water, extracted with 2x50 ml washings of ether, acidified to have a pH of 1 and stirred for 2 hours at 0° C. The resulting precipitate was collected on a glass filter to give 1.30g (87% yield) of Fmoc-(S)-TFNV. mp: 131° C., $^1$H NMR (CDCl3) δ1.6-2.0 (m, 2H), 2.0-2.36 (m, 2H), 4.18 (t, J=6.0 Hz, 1H), 4.40 (d, J=7.0 Hz, 2H) 4.56 (m, 1H), 5.21 (d, J=8.6 Hz, 1H), 7.2-7.8 (m, 8H); $^{19}$F NMR (CDCl3/CF3Cl) δ- 73.7; IRcm$^4$ 3325.2 (m), 2918.9 (s), 1690.2 (m), 1533.7 (s), 1458.1 (s), 1376.6 (m), 1255.1 (m); $[\alpha]_D^{20}$ −14.8° (c 0.54, EtOH).

Example V

N-Fluorenylmethoxycarbonyl-(R)-5,5,5-trifluoronorvaline (Fmoc-(R)-TFNV)

(R)-TFNV (650 mg, 3.8 mmol) was dissolved in 20 ml of water together with sodium carbonate (1.01 mg, 9.5 mmol). Fmoc-Cl (938 mg, 3.8 mmol) in 10 ml of dioxane was added dropwise to the aqueous solution under vigorous stirring at 0° C. over a period of 30 minutes. The stirring was continued for 4 hours at 0° C., 40 ml of water was added to dissolve some precipitation. The reaction mixture was stirred for 15 hours at room temperature, then poured into 300 ml of water, extracted with 2×50 ml of ether, acidified to have a pH of 1 and stirred for 2 hours at 0° C. The resulting precipitate was collected on a glass filter to give Fmoc-(R)-TFNV mp: 131° C., $^1$H NMR (CDCl3) δ1.6-2.0 (m, 2H), 2.0-2.36 (m, 2H), 4.18 (t, J=6.0 Hz, 1H), 4.40 (d, J=7.0 Hz, 2H) 4.56 (m, 1H), 5.21 (d, J=8.6 Hz, 1H), 7.2-7.8 (m, 8H); $^{19}$F NMR (CDCl3/CF3Cl) δ- 73.7; IRcm$^{-1}$3325.2 (m), 2918.9 (s), 1690.2 (m), 1533.7 (s), 1458.1 (s), 1376.6 (m), 1255.1 (m); $[\alpha]_D^{20}$ +14.8° (c 0.54, EtOH).

Example VI

Preparation of Trifluoronorvaline Met-enkephalins (i) Preparation of TFA Tyr-Gly-(L)-TFNV-Phe-Met-NH2 SEQ ID NO:6

Fmoc protected Met-OPfp (0.25 mmol) was reacted with 0.1 mmol of 2,4-dimethoxybenzhydrilamine resin in the presence of 0.25 mmol of diisopropylcarbodiimide and 0.1 mmol of 0.5M DMF solution to form an Fmoc-Met-NH-Resin complex. This was followed by washing with methanol (3 ml×3). The Fmoc group was then removed by exposure to 3 ml of a mixture of piperidine-DMF (1:1) for about 9 minutes.

Next, 0.25 mmol of Fmoc protected Phe-OPfp was added to the reaction mixture and allowed to react for 2 hours. The Fmoc-Phe-OPfp reacted with the Met-NH-Resin complex to form an Fmoc-Phe-Met-NH-Resin complex. This was followed by a washing with methanol (3 ml×3). The Fmoc protecting group was then removed by exposure to 3 ml of a mixture of piperidine-DMF (1:1) for about 9 minutes.

Next, 0.25 mmol of Fmoc protected (L)-TFNV-OPfp was added to the reaction mixture and allowed to react for 2 hours. The Fmoc-(L)-TFNV reacted with the Phe-Met-NH-Resin complex to form an Fmoc-(L)-TFNV-Phe-Met-NH-Resin complex. This was followed by washing with methanol (3 ml×3). The Fmoc protecting group was removed by exposure to 3 ml of a mixture of piperidine-DMF (1:1) for about 9 minutes.

Fmoc protected Gly-OPfp (0.25 mmol) was added to the reaction mixture and allowed to react for 2 hours. The Fmoc-Gly-OPfp reacted with the (L)-TFNV-Phe-Met-NH-Resin complex to form an Fmoc-Gly-(L)-TFNV-Phe-Met-NH-Resin complex SEQ ID NO:10. This was followed by a washing methanol (3 ml×3). The Fmoc protecting group was removed by exposure to 3 ml of a mixture of piperidine-DMF (1:1) for about 9 minutes.

Finally, Fmoc protected Tyr-OPfp (0.25 mmol) was added to the reaction mixture and allowed to react for 2 hours. The Fmoc-Tyr-OPfp reacted with the Gly-L-TFNV-Phe-Met-NH-Resin complex SEQ ID NO:11 to form an Fmoc-Tyr-Gly-(L)-TFNV-Phe-Met-NH-Resin complex SEQ ID NO:12. This was followed by washing with methanol (3 ml×3). The Fmoc protecting group was removed by exposure to 3 ml of the mixture of piperidine-DMF (1:1) for about 9 minutes.

After all the coupling and the deprotecting reactions had occurred, the resulting reaction mixture was treated with trifluoroacetic acid for 16 hours. This was followed by removal of the resin, purification and lyophilization to yield TFA Tyr-Gly-(L)-TFNV-Phe-Met-NH2 SEQ ID NO:6 as a pale yellow powder.

(ii) Preparation of TFA Tyr-(L)-TFNV-Gly-Phe-Met-NH2 SEQ ID NO:8

Fmoc protected Met-OPfp (0.25 mmol) was reacted with 0.1 mmol of 2,4-dimethoxybenzhydrilamine resin in the presence of 0.25 mmol of diisopropylcarbodiimide and 0.1 mmol of 0.5M DMF solution to form an Fmoc-Met-NH-Resin complex. This was followed by washing with methanol (3 ml×3). The Fmoc group was then removed by exposure to 3 ml of a mixture of piperidine-DMF (1:1) for about 9 minutes.

Fmoc protected Phe-OPfp (0.25 mmol) was added to the reaction mixture and allowed to react for 2 hours. The Fmoc-Phe-OPfp reacted with the Met-NH-Resin complex to form an Fmoc-Phe-Met-NH-Resin complex. This was followed by a washing with methanol (3 ml×3). The Fmoc protecting group was then removed by exposure to 3 ml of a mixture of piperidine-DMF (1:1) for about 9 minutes.

Fmoc protected Gly-OPfp (0.25 mmol) was added to the reaction mixture and allowed to react for 2 hours. The Fmoc-Gly-OPfp reacted with the Phe-Met-NH-Resin complex to form an Fmoc-Gly-Phe-Met-NH-Resin complex. This was followed by a washing with methanol (3 ml×3). The Fmoc protecting group was removed by exposure to 3 ml of a mixture of piperidine-DMF (1:1) for about 9 minutes.

Next, 0.25 mmol of Fmoc protected (L)-TFNV-OPfp was added to the reaction mixture and allowed to react for 2 hours. The Fmoc-(L)-TFNV-OPfp reacted with the Gly-Phe-Met-NH-Resin complex to form an Fmoc-(L)-TFNV-Gly-Phe-Met-NH-Resin complex SEQ ID NO:13. This was followed by washing with methanol (3 ml×3). The Fmoc protecting group was removed by exposure to 3 ml of the mixture of piperidine-DMF (1:1) for about 9 minutes.

Finally, Fmoc protected Tyr-OPfp (0.25 mmol) was added to the reaction mixture and allowed to react for 2 hours. The Fmoc-Tyr-Opfp reacted with the (L)-TFNV-Gly-Phe-Met-NH-Resin complex SEQ ID NO:14 to form an Fmoc-Tyr-(L)-TFNV-Gly-Phe-Met-NH-Resin complex SEQ ID NO:15. This was followed by washing with methanol (3 ml×3). The Fmoc protecting group was removed by exposure to 3 ml of the mixture of piperidine-DMF (1:1) for about 9 minutes.

After all the coupling and the deprotecting reactions had occurred, the resulting reaction mixture was treated with trifluoroacetic acid for 16 hours. This was followed by removal of the resin, purification and lyophilization to yield TFA Tyr-(L)-TFNV-Gly-Phe-Met-NH$_2$ SEQ ID NO:8 as a pale yellow powder.

(iii) Preparation of TFA Tyr-Gly-(D)-TFNV-Phe-Met-NH$_2$ SEQ ID NO:20

Fmoc protected Met-OPfp (0.25 mmol) was reacted with 0.1 mmol of 2,4-dimethoxybenzhydrilamine resin in the presence of 0.25 mmol of diisopropylcarbodiimide and 0.1 mmol of 0.5M DMF solution to form an Fmoc-Met-NH-Resin complex. This was followed by washing with methanol (3 ml×3). The Fmoc group was then removed by exposure to 3 ml of a mixture of piperidine-DMF (1:1) for about 9 minutes.

Next, 0.25 mmol of Fmoc protected Phe-OPfp was added to the reaction mixture and allowed to react for 2 hours. The Fmoc-Phe-OPfp reacted with the Met-NH-Resin complex to form an Fmoc-Phe-Met-NH-Resin complex. This was followed by a washing with methanol (3 ml×3). The Fmoc protecting group was then removed by exposure to 3 ml of a mixture of piperidine-DMF (1:1) for about 9 minutes.

Next, 0.25 mmol of Fmoc protected (D)-TFNV-Opfp was added to the reaction mixture and allowed to react for 2 hours. The Fmoc-D-TFNV-OPfp reacted with the Phe-Met-NH$_2$-Resin complex to form an Fmoc-(D)-TFNV-Phe-Met-NH-Resin complex SEQ ID N O:23. This was followed by washing with methanol (3 ml×3). The Fmoc protecting group was removed by exposure to 3 ml of the mixture of piperidine-DMF (1:1) for about 9 minutes.

Fmoc protected Gly-OPfp (0.25 mmol) was added to the reaction mixture and allowed to react for 2 hours. The Fmoc-Gly-OPfp reacted with the (D)-TFNV-Phe-Met-NH-Resin complex to form an Fmoc-Gly-(D)-TFNV-Phe-Met-NH-Resin complex SEQ ID NO:24. This was followed by a washing with methanol (3 ml×3). The Fmoc protecting group was removed by exposure to 3 ml of a mixture of piperidine-DMF (1:1) for about 9 minutes.

Finally, 0.25 mmol of Fmoc protected Tyr-OPfp was added to the reaction mixture and allowed to react for 2 hours. The Fmoc-Tyr-OPfp reacted with the Gly-(D)-TFNV-Phe-Met-NH-Resin complex SEQ ID NO:25 to form an Fmoc-Tyr-Gly-(D)-TFNV-Phe-Met-NH-Resin complex SEQ ID NO:26. This was followed by washing with methanol (3 ml×3). The Fmoc protecting group was removed by exposure to 3 ml of the mixture of piperidine-DMF (1:1) for about 9 minutes.

After all the coupling and the deprotecting reactions had occurred, the resulting reaction mixture was treated with trifluoroacetic acid for 16 hours. This was followed by removal of the resin, purification and lyophilization to yield TFA Tyr-Gly-(D)-TFNV-Phe-Met-NH$_2$ SEQ ID NO:20 as a pale yellow powder.

(iv) Preparation of TFA Tyr-Gly-(D)-TFNV-Phe-Met-NH$_2$ SEQ ID NO:20

Fmoc protected Met-OPfp (0.25 mmol) was reacted with 0.1 mmol of 2,4-dimethoxybenzhydrilamine resin in the presence of 0.25 mmol of diisopropylcarbodiimide and 0.1 mmol of 0.5M DMF solution to form an Fmoc-Met-NH-Resin complex. This was followed by washing with methanol (3 ml×3). The Fmoc group was then removed by exposure to 3 ml of a mixture of piperidine-DMF (1:1) for about 9 minutes.

Next, 0.25 mmol of Fmoc protected Phe-OPfp (0.25 mmol) was added to the reaction mixture and allowed to react for 2 hours. The Fmoc-Phe-OPfp reacted with the Met-NH-Resin complex to form an Fmoc-Phe-Met-NH-Resin complex. This was followed by a washing with methanol (3 ml×3). The Fmoc protecting group was then removed by exposure to 3 ml of a mixture of piperidine-DMF (1:1) for about 9 minutes.

Next, 0.25 mmol of Fmoc protected (D)-TFNV-OPfp was added to the reaction mixture and allowed to react or 2 hours. The Fmoc-(D)-TFNV-OPfp reacted with the Phe-Met-NH-Resin complex to form an Fmoc-(D)-TFNV-Phe-Met-NH-Resin complex SEQ ID NO:23. This was followed by washing with methanol (3 ml×3). The Fmoc protecting group was removed by exposure to 3 ml of the mixture of piperidine-DMF (1:1) for about 9 minutes.

Fmoc protected Gly-OPfp (0.25 mmol) was added to the reaction mixture and allowed to react for 2 hours. The Fmoc-Gly-OPfp reacted with the (D)-TFNV-Phe-Met-NH-Resin complex to form an Fmoc-Gly-(D)-TFNV-Phe-Met-NH-Resin complex SEQ ID NO:24. This was followed by a washing with methanol (3 ml×3). The Fmoc protecting group was removed by exposure to 3 ml of a mixture of piperidine-DMF (1:1) for about 9 minutes.

Finally, 0.25 mmol of Fmoc protected Tyr-OPfp was added to the reaction mixture and allowed to react for 2 hours. The Fmoc-Tyr-OPfp reacted with the Gly-(D)-TFNV-Phe-Met-NH-Resin complex SEQ ID NO:25 to form an Fmoc-Tyr-Gly-(D)-TFNV-Phe-Met-NH-Resin complex SEQ ID NO:26. This was followed by washing with methanol (3 ml×3). The Fmoc protecting group was removed by exposure to 3 ml of the mixture of piperidine-DMF (1:1) for about 9 minutes.

After all the coupling and the deprotecting reactions had occurred, the resulting reaction mixture was treated with trifluoroacetic acid for 16 hours. This was followed by removal of the resin, purification and lyophilization to yield TFA Tyr-Gly-(D)-TFNV-Phe-Met-NH$_2$ SEQ ID NO:20 as a pale yellow powder.

(v) Preparation of Tyr-Gly-(L)-TFNV-Phe-Met-NH$_2$ SEQ ID NO:16

Fmoc protected Met-OPfp (0.25 mmol) was reacted with 0.1 mmol of 2,4-dimethoxybenzhydrilamine resin in the presence of 0.25 mmol of diisopropylcarbodiimide and 0.1 mmol of 0.5M DMF solution to form an Fmoc-Met-NH-Resin complex. This was followed by washing with methanol (3 ml×3). The Fmoc group was then removed by exposure to 3 ml of a mixture of piperidine-DMF (1:1) for about 9 minutes.

Next, 0.25 mmol of Fmoc-Phe-OPfp was added to the reaction mixture and allowed to react for 2 hours. The Fmoc-Phe-OPfp reacted with the Met-NH-Resin complex to form an Fmoc-Phe-Met-NH-Resin complex. This was followed by a washing with methanol (3 ml×3). The Fmoc protecting group was then removed by exposure to 3 ml of a mixture of piperidine-DMF (1:1) for about 9 minutes.

Next, 0.25 mmol of Fmoc-(L)-TFNV-OPfp was added to the reaction mixture and allowed to react for 2 hours. The Fmoc-(L)-TFNV-OPfp reacted with the Phe-Met-NH-Resin complete to form an Fmoc-(L)-TFNV-Phe-Met-NH-Resin complex SEQ ID No:27. This was followed by washing with methanol (3 ml×3). The Fmoc protecting group was removed by exposure to 3 ml of the mixture of piperidine-DMP (1:1) for about 9 minutes.

Fmoc-Gly-OPfp (0.25 mmol) was added to the reaction mixture and allowed to react for 2 hours. The Fmoc-Gly-OPfp coupled with the L-TFNV-Phe-Met-NII-Resin complex to form an Fmoc-Gly-(L)-TFNV-Phe-Met-NH-Resin complex SEQ ID NO:10. This was followed by a washing with methanol (3 ml×3). The Fmoc protecting group was removed by exposure to 3 ml of a mixture of piperidine-DMF (1:1) for about 9 minutes.

Finally, Fmoc-Tyr-OPfp (0.25 mmol) was added to the reaction mixture and allowed to react for 2 hours. The Fmoc-Tyr-OPfp coupled with the Gly-(L)-TFNV-Phe-Met-NH-Resin complex SEQ ID NO:11 to form an Fmoc-Tyr-Gly-(L)-TFNV-Phe-Met-NII-Resin complex SEQ ID NO:12. This was followed by washing with methanol (3 ml×3). The Fmoc protecting group was removed by exposure to 3 ml of the mixture of piperdine-DMF (1:1) for about 9 minutes.

After all the coupling and the deprotecting reactions had occurred, the resulting reaction mixture was treated with trifluoroacetic acid for 16 hours. This was followed by removal of the resin, purification and lyophilization to yield TFA Tyr-Gly-L-TFNV-Phe-Met-NH$_2$ as a pale yellow powder.

Tyr-(D)-TFNV-Gly-Phe-Met-NH$_2$ SEQ ID NO:6 was obtained with an ion-exchange column (Dowex-50) using 0.1N aqueous ammonia as a the eluant.

EXAMPLE VII

The analgesic activity of trifluoronorvaline containing Met-enkephalin derivatives was evaluated in an experimental procedure using ddY male mice (5 weeks old). The mice were given an intraperitoneal injection (10 ml/kg) of a 0.7% acetic acid solution. Ten minutes later, 20 ml of a solution of trifluoronorvaline containing Met-Enkephalin derivatives ($2\times10^{-15}$ $2\times10^{-7}$M) were administered intracerebroventricularly using saline as the vehicle (20 µl/mouse). After an additional 10 minutes had passed, the writhing reaction was determined to establish the analgesic activity. The mice in the control group were given the same intraperitoneal injection of 0.7% acetic acid solution and were administered 20 µl of saline intracerebroventricularly ten minutes thereafter.

The inhibition ratio was calculated as follows:

$$\text{Inhibition ratio (\%)} = \frac{\text{Writhing number in tested group}}{\text{Writhing number of control group}} \times 100$$

The results are illustrated in graphic form in FIG. 1.

The inhibition ratio (ED$_{50}$) is based on the concentration of tested compounds which inhibited 50% of the writhing. The inhibition ratios are listed in Table 2.

TABLE 2

| Analgesic Activity (icv Administration in Mouse) | |
|---|---|
| Compound | ED$_{50}$ mol/mouse |
| Met-enkephalin SEQ ID NO:1 | $7.0 \times 10^{-8}$ |
| TFA Tyr—Gly-L-TFNV-Phe—Met—NH$_2$ SEQ ID NO:6 | $2.2 \times 10^{-8}$ |
| TFA Tyr-L-TFNV-Cly—Phe—Met—NH$_2$ SEQ ID NO:8 | $2.5 \times 10^{-8}$ |
| TFA Tyr-D-TFNV-Gly—Phe—Met—NH$_2$ SEQ ID NO:19 | $4.3 \times 10^{-13}$ |

While there have been described what are presently provided in the preferred embodiments of the invention, those skilled in the art will realize that changes and modifications may be made thereto without departing from the spirit of the invention, and it is intended to claim all changes and modifications as fall within the scope of the present invention.

---

What is claimed is:

1. A compound of the formula Tyr-$A_1$-$A_2A_3A_4$ SEQ ID NO:5 and the acid addition salts thereof, in which Tyr is L-Tyrosine; at least one of $A_1$ or $A_2$ is a glycine and that which is not a glycine is an optically active compound of the formula:

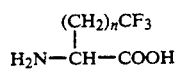

wherein n is 2 or 3 $A_3$ is L-Phenylalanine, or N-methyl-(L)phenylalanine; and $A_4$ is L-Methionine, L-Met-ol or L-Met-$NH_2$.

2. The compound of claim 1 wherein the acid of the acid addition salt is selected from the group consisting of organic and inorganic acids.

3. The compound of claim 2 wherein the acid is selected from the group consisting of hydrochloric acid, sulfuric acid, citric acid, lactic acid, oxalic acid, maleic acid, succinic acid, tartaric acid, acetic acid, trifluoroacetic acid, salicylic acid and ascorbic acid.

4. The compound of claim 2 wherein the acid is trifluoroacetic acid.

5. A compound according to claim 1, selected from the group consisting of:

| | |
|---|---|
| SEQ ID NO:6 | TFA.Tyr—Gly-(L)-TFNV-Phe—Met—$NH_2$; |
| SEQ ID NO:7 | TFA.Tyr-(L)-TFNV-Gly—Phe—Met; |
| SEQ ID NO:8 | TFA.Tyr-(L)-TFNV-Gly—Phe—Met—$NH_2$; |
| SEQ ID NO:19 | TFA.Tyr-(D)-TFNV-Gly—Phe—Met—$NH_2$; |
| SEQ ID NO:20 | TFA.Tyr—Gly-(D)-TFNV-Phe—Met—$NH_2$; |
| SEQ ID NO:9 | TFA.Tyr—Gly-(L)-TFNV-Phe—Met; |
| SEQ ID NO:22 | Tyr-(D)-TFNV-Gly—Phe—Met—$NH_2$; and |
| SEQ ID NO:21 | TFA.Tyr-(D)-TFNV-Gly—Phe—Met. |

6. The compound of claim 1 wherein $A_1$ is glycine, n is 2 and $A_2$ is (L)-TFNV, $A_3$ is Phe and $A_4$ is Met-$NH_2$.

7. The compound of claim 1 wherein n is 2 and $A_1$ is (L)-TFNV, $A_2$ is Glycine, $A_3$ is Phe and $A_4$ is Met.

8. The compound of claim 1 wherein n is 2 and $A_1$ is (L)-TFNV, $A_2$ is Glycine, $A_3$ is Phe and $A_4$ is Met-$NH_2$.

9. The compound of claim 1 wherein n is 2 and $A_1$ is (D)-TFNV, $A_2$ is Glycine, $A_3$ is Phe and $A_4$ is Met-$NH_2$.

10. The compound of claim 1 wherein $A_1$ is Glycine, n is 2 and $A_2$ is (D)-TFNV, $A_3$ is Phe and $A_4$ is Met-$NH_2$.

11. The compound of claim 1 wherein $A_1$ is Glycine, n is 2 and $A_2$ is (L) TFNV, $A_3$ is Phe and $A_4$ is Met-$NH_2$.

12. The compound of claim 1 in combination with a pharmaceutically acceptable carrier.

13. The compound of claim 12 wherein the pharmaceutically acceptable carrier is selected from the group consisting of dextrose solutions, sodium chloride solutions (saline), sterile water and buffer solutions.

14. A method of treating pain which comprises providing an analgesically effective dose to a recipient of at least one compound of the formula Tyr-$A_1$-$A_2$-$A_3$-$A_4$ SEQ ID NO:5 and the acid addition salts thereof, in which Tyr is L-Tyrosine; at least one of $A_1$ or $A_2$ is a glycine and that which is not a glycine is an optically active compound of the formula:

$$\underset{H_2N-CH-COOH}{\overset{(CH_2)_nCF_3}{|}}$$

wherein n is 2 or 3; $A_3$ is L-Phenylalanine, or N-methyl-(L)-phenylalanine; and $A_4$ is L-Methionine, L-Met-ol or L-Met-$NH_2$.

15. The method of claim 12 wherein the compound is selected from the group consisting of

| | |
|---|---|
| SEQ ID NO:6 | TFA.Tyr—Gly-(L)-TFNV-Phe—Met—$NH_2$; |
| SEQ ID NO:7 | TFA.Tyr-(L)-TFNV-Gly—Phe—Met; |
| SEQ ID NO:8 | TFA.Tyr-(L)-TFNV-Gly—Phe—Met—$NH_2$; |
| SEQ ID NO:19 | TFA.Tyr-(D)-TFNV-Gly—Phe—Met—$NH_2$; |
| SEQ ID NO:20 | TFA.Tyr—Gly-(D)-TFNV-Phe—Met—$NH_2$; |
| SEQ ID NO:9 | TFA.Tyr—Gly-(L)-TFNV-Phe—Met; |
| SEQ ID NO:22 | Tyr-(D)-TFNV-Gly—Phe—Met—$NH_2$; and |
| SEQ ID NO:21 | TFA.Tyr-(D)-TFNV-Gly—Phe—Met. |

16. The method of claim 15 wherein the compound is provided in combination with a pharmaceutically acceptable carrier.

17. The method of claim 15 wherein the pharmaceutically acceptable carrier is selected from the group consisting of dextrose solutions, sodium chloride solutions (saline), sterile water and buffer solutions.

18. The method of claim 15 wherein the compound is provided intramuscularly, subcutaneously or orally.

19. The method of claim 15 wherein the dosage is provided intramuscularly and the dosage ranges from about 4 µg to about 17 µg per kilogram bodyweight of the recipient.

20. The method of claim 18 wherein the dosage is provided intramuscularly and ranges from about 8 µg to about 17 µg per kilogram bodyweight of the recipient.

21. The method of claim 18 wherein the dosage is provided subcutaneously and ranges from about 7 µg to about 14 µg per kilogram bodyweight of the recipient.

22. The method of claim 18 wherein the dosage is provided subcutaneously and ranges from about 8 µg to about 17 µg per kilogram bodyweight of the recipient.

23. The method of claim 18 wherein the compound is provided orally and the dose ranges from about 20 ng to about 50 ng per kilogram bodyweight of the recipient.

24. The method of claim 18 wherein the compound is provided orally and the dose ranges from about 15 ng to about 45 ng per kilogram bodyweight of the recipient.

* * * * *

UNITED STATES PATENT AND TRADEMARK OFFICE
CERTIFICATE OF CORRECTION

PATENT NO. : 5,276,137          Page 1 of 9
DATED      : January 4, 1994
INVENTOR(S): Ojima, et al.

It is certified that error appears in the above-indentified patent and that said Letters Patent is hereby corrected as shown below:

Column 1, Line 41    now reads "Petpides", should read --Peptides--.

Column 4, Line 49    now reads "DFM", should read --DMF--.

Column 6, Line 48    now reads "1.86 ($\epsilon$,3H), should read --1.86(S,3H)--.

Column 6, Line 61    now reads "(15mg, 850 unit/mg)", should read --(45 mg, 850 unit/mg)--.

Column 6, Line 67    now reads "$[\alpha]_D^{20}$ + 7.2°", should read --$[\alpha]^{20}_D$ + 7.2°--.

Column 7, Line 18    now reads "$[\alpha]_D^{20}$ - 6.8°", should read --$[\alpha]^{20}_D$ - 6.8°--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 7, Line 44   now reads "$[\alpha]_D^{20} - 14.8°$", should read --$[\alpha]^{20}_D - 14.8°$--.

Column 7, Line 68   now reads "$[\alpha]_D^{20} + 14.8°$", should read --$[\alpha]^{20}_D + 14.8°$--.

Column 9, Line 25   now reads "Tyr-Opfp reacted", should read --Tyr-OPfp reacted--.

Column 9, Line 61   now reads "SEQ ID N O: 23", should read --SEQ ID NO:23--.

Column 10, Line 44  now reads "react or 2 hours.", should read --reacted for 2 hours.--.

Column 11, Line 29  now reads "complete", should read --complex--.

Column 12, Line 43  now reads "-TFNV-Cly-", should read -- -TFNV-Gly- --.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 12, Line 45  In Table 2 under SEQ ID NO: 19 insert
--TFA Tyr-Gly-D-TFNV-Phe-Met-$NH_2$
SEQ ID NO:20.

IN THE SEQUENCE LISTING

Column 13, SEQ ID NO: 3 now reads  "$R^3$
            R1-Tyr
            R2", should read  --R3
             |
             R1-Tyr-
             |
             R2--.

Column 13, SEQ ID NO: 3 now reads "aralkyloxycarbonyl alkoxycarbonyl", should read --aralkyloxycarbonyl or alkoxycarbonyl--.

UNITED STATES PATENT AND TRADEMARK OFFICE
CERTIFICATE OF CORRECTION

PATENT NO. : 5,276,137  
DATED : January 4, 1994  
INVENTOR(S) : Ojima, et al.

Page 4 of 9

It is certified that error appears in the above-indentified patent and that said Letters Patent is hereby corrected as shown below:

Column 15, SEQ ID NO: 5 now reads     "nCF3  
                        H2N-CH-COOH",  
    should read   --$nCF_3$  
                        |  
                        $H_2N$-CH-COOH--.

Column 15, SEQ ID NO: 6 now reads "/note="TFAyTyr"", should read --/note="TFA·Yyr"--.

Column 15 SEQ ID NO: 6 now reads "/note="Met-NH2"", should read --/note="Met-$NH_2$"--.

Column 15 SEQ ID NO: 7 now reads "/note="TFAyTyr"", should read --/note="TFA·Yyr"--.

Column 17 SEQ ID NO: 8 now reads "/note="TFAyTyr"", should read --/note="TFA·Yyr"--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 17 SEQ ID NO: 8 now reads "/note="Met-NH2"", should read --/note="Met-NH$_2$"--.

Column 17 SEQ ID NO: 9 now reads "/note="TFAyTyr"", should read --/note="TFA·Yyr"--.

Column 19 SEQ ID NO: 12 now reads "/note="FmocyTyr"", should read --/note="Fmoc·Tyr--.

Column 23 SEQ ID NO: 17 now reads    "N-(D)-Ser, wherein R2 is R2"

should read    --N-(D)-Ser, wherein R2 is
|
R2--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 23 SEQ ID NO: 17 now reads        "/note="N-Phe, wherein R3 is R3"

should read    --/note="N-Phe, wherein R3 is
$$\overset{|}{R_3}$$
--.

Column 23 SEQ ID NO: 17 now reads        "/note="N-(D)-Ser-X, wherein R4 R4"

should read    --/note="N-(D)-Ser-X, wherein R4
$$\overset{|}{R_4}$$
--.

Column 23 SEQ ID NO: 17 now reads        "and X is OH, NH2 or NHCnH2n where", should read    --and X is OH, $NH_2$ or $NHC_nH_{2n+1}$ where--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 23 SEQ ID NO: 17 now reads "where R3 is a hydrogen lower alkyl", should read --where R3 is a hydrogen or lower alkyl--.

Column 23 SEQ ID NO: 18, line 20, now reads "/note="B-NH-$C_nH2_n$-Y," should read --/note="B-NH-$C_nH_{2n}$-Y,--.

Column 23 SEQ ID NO: 18 now reads "group-NHSO2X,", should read --group NHSO X,--

Column 23 SEQ ID NO: 18 now reads "an alpha or b", should read --an alpha or beta--.

Column 23 SEQ ID NO: 18 now reads "polycyclic group cho", should read --polycyclic group chosen--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 23 SEQ ID NO: 19 now reads "/note="TFAyTyr"", should read --/note="TFA·Tyr"--.

Column 25 SEQ ID NO: 19 now reads "/note="Met-NH2"", should read --/note="Met-NH$_2$"--.

Column 25 SEQ ID NO: 20 now reads "/note="TFAyTYR"", should read --/note="TFA·Tyr"--.

Column 25 SEQ ID NO: 20 now reads "/note="Met-NH2"", should read --/note="Met-NH$_2$"--.

Column 25 SEQ ID NO: 21 now reads "/note="TFAyTyr"", should read --/note="TFA·Tyr"--.

UNITED STATES PATENT AND TRADEMARK OFFICE
CERTIFICATE OF CORRECTION

PATENT NO. : 5,276,137
DATED : January 4, 1994
INVENTOR(S) : Ojima, et al.

It is certified that error appears in the above-indentified patent and that said Letters Patent is hereby corrected as shown below:

Column 25 SEQ ID NO: 22 now reads "/note="Met-NH2"", should read --/note="Met-NH$_2$"--.

IN THE CLAIMS

Column 29, Line 50 now reads "Tyr-A$_1$-A$_2$A$_3$A$_4$", should read --Tyr-A$_1$-A$_2$-A$_3$-A$_4$--.

Signed and Sealed this

Sixth Day of June, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO : 5,276,137
DATED : January 4, 1994
INVENTOR(S) : Ojima, et. al.

It is certified that error appears in the above-identified patent and that said Letters Patent is hereby corrected as shown below:

Column 23, SEQ ID NO: 18, line 20, now reads "group-NHSO2X,", should read --group-$NHSO_2X$,--

This certificate supersedes Certificate of Correction issued June 6, 1995.

Signed and Sealed this

Twenty-seventh Day of June, 1995

*Attest:*

BRUCE LEHMAN

*Attesting Officer*     *Commissioner of Patents and Trademarks*